United States Patent [19]

Tsay et al.

[11] Patent Number: 4,663,160
[45] Date of Patent: May 5, 1987

[54] VACCINES FOR GRAM-NEGATIVE BACTERIA

[75] Inventors: Grace C. Tsay, Moraga; Michael S. Collins, Richmond, both of Calif.

[73] Assignee: Miles Laboratories, Inc., Elkhart, Ind.

[21] Appl. No.: 475,415

[22] Filed: Mar. 14, 1983

[51] Int. Cl.$^4$ .................. A61K 39/40; A61K 39/104; A61K 39/02
[52] U.S. Cl. ...................... 424/87; 424/92; 424/85; 424/88
[58] Field of Search ...................... 424/88, 92, 85-87

[56] References Cited

U.S. PATENT DOCUMENTS

| | | | |
|---|---|---|---|
| 3,987,164 | 10/1976 | Homma et al. | 424/92 |
| 4,083,959 | 4/1978 | Homma et al. | 424/92 |
| 4,110,432 | 8/1978 | Wilkinson et al. | 424/88 |
| 4,157,389 | 6/1979 | Homma et al. | 424/92 |
| 4,185,090 | 1/1980 | McIntire | 424/92 |
| 4,285,936 | 9/1981 | Pier et al. | 424/92 |
| 4,356,170 | 10/1982 | Jennings et al. | 424/92 |
| 4,372,883 | 2/1983 | Matuhashi et al. | 424/92 |

OTHER PUBLICATIONS

Jennings, H. et al., J. Immunology, vol. 127, pp. 1211-1218, 1981.
Schneerson, R. et al., J. Experimental Medicine, vol. 132, pp. 361-376, 1980.
Chemical Abstracts, vol. 94, Abstract No. 145220x, 1981.

*Primary Examiner*—Blondel Hazel
*Attorney, Agent, or Firm*—Lester E. Johnson; Pamela A. Simonton

[57] ABSTRACT

An immunizing composition is disclosed and comprises a detoxified polysaccharide from a gram-negative bacterium covalently coupled to a detoxified protein from said gram-negative bacterium by means of a 4-12 carbon moiety. To prepare the above immunizing agent, the lipid A portion of lipopolysaccharide from a gram-negative bacterium is separated to give a detoxified polysaccharide. Reactive aldehyde groups are generated on the detoxified polysaccharide by selective oxidation. The detoxified polysaccharide is then covalently coupled to a detoxified protein from said gram-negative bacterium by means of a 4-12 carbon moiety having functionalities reactive to the aldehyde groups on the detoxified polysaccharide and to the carboxylic groups on the detoxified protein.

16 Claims, No Drawings

VACCINES FOR GRAM-NEGATIVE BACTERIA

BACKGROUND OF THE INVENTION

1. Field of the Invention

This invention relates to and has among its objects novel non-toxic immunizing compositions against gram-negative bacteria and novel methods for their preparation. It is a particular object of the invention to prepare an immunizing composition effective against *Pseudomonas aeruginosa* infections. Further objects of the invention will be evident from the following description wherein parts and percentages are by weight unless otherwise specified.

2. Description of the Prior Art

Gram-negative bacteria have two cell envelope membranes separated by a single thin layer of peptidoglycan. The inner or cytoplasmic membrane contains all known active transport systems and many of the cell envelop enzymes. The outer membrane is distinguished by a unique component lipopolysaccharide (lipid A plus polysaccharide) and a unique set of proteins. The O antigen-specific polysaccharide endows the particular bacterium with its main serological specificity. There is also a core polysaccharide, common to gram-negative bacteria, which is linked to a lipid component (lipid A). These complexes of lipid A, polysaccharide, and protein are antigenic and also exert toxic reactions in humans, thus being considered as endotoxins.

Vaccines containing lipopolysaccharides (LPS) from gram-negative bacteria have been used for immunization of humans against infection. The vaccines may comprise killed cells, cell lysate, or purified LPS; however, many are toxic.

Although infection with *Pseudomonas aeruginosa* (*P. aeruginosa*) is not common among the general population, *P. aeruginosa* infection is encountered very frequently in certain susceptible groups of patients. Burn victims and immunosuppressed cancer patients have been identified as having an unusually high risk of acquiring severe, and sometimes fatal, *P. aeruginosa* infection. *P. aeruginosa* infections are usually acquired during a hospital stay, not at home.

Antibiotics have been used to treat patients with *P. aeruginosa* infections. However, antibiotic treatment is very expensive, effectiveness is often uncertain, and organisms continue to develop resistance to antibiotics.

Vaccines have been prepared for a number of pathogenic bacteria, including *P. aeruginosa*. For example, U.S. Pat. No. 4,157,389 discloses a three component mixed vaccine against infections caused by *P. aeruginosa* which comprises as the antigens an infection-protective common antigen, Original Endotoxin Protein obtained from *P. aeruginosa*, an elastase toxoid obtained from *P. aeruginosa* and a protease toxoid obtained from *P. aeruginosa*.

Toxoids derived from protease and elastase of *P. aeruginosa* which are effective to prevent infections caused by *P. aeruginosa* are described in U.S. Pat. No. 4,160,023.

U.S. Pat. No. 3,987,164 discloses vaccine preparations comprising the cell wall protein component of *P. aeruginosa* as an active ingredient in a prophylactic pharmaceutical preparation.

Mink infection caused by *P. aeruginosa* can be prevented according to U.S. Pat. No. 4,096,245 by administering to mink a prophylactic preparation in the form of vaccine whose effective component mainly consists of protein and a small amount of lipid and sugar derived from *P. aeruginosa*.

Original endotoxin protein derived from *P. aeruginosa* is disclosed in U.S. Pat. No. 4,079,126. In the patented method of preparation the original endotoxin protein is processed with either proteolytic enzyme or reductant or further processed with proteolytic enzyme after it has been treated with reductant.

A bacterial endotoxin LPS of reduced toxicity covalently coupled to a protein antigen is described in U.S. Pat. No. 4,185,090. The coupling was effected by reaction with haloacylhalide. LPS acylated with an anhydride of a dibasic acid is detoxified; in combination with endotoxin polysaccharide covalently coupled to protein antigen it developed synergistic immunogenic effects.

In U.S. Pat. No. 4,285,936 a method is taught for isolating a non-toxic, high molecular weight polysaccharide antigen from the crude slime of a *P. aeruginosa* culture, and a method for inducing immunity in a host to said live organisms is described. Initially, bacterial cells are separated from the slime, which is dissolved in a phosphate buffer solution. After removal of dissolved contaminating nucleic acids, a lipid A portion of the contaminating LPS constituent is removed and precipitated by acetic acid hydrolysis. The remaining lipids are extracted with chloroform. Nearly all of the residual nucleic acids are then removed by digestion with nucleases, and the remaining protein extracted with phenol. The aqueous and phenol layers are separated, and the aqueous layer applied to a gel filter to isolate the polysaccharide antigen by column chromatography. The polysaccharide antigen was non-toxic and highly effective in inducing an immune response to the organism in a host.

SUMMARY OF THE INVENTION

We have discovered an immunizing composition comprising a detoxified protein derived from a gram-negative bacterium covalently coupled by means of a 4-12 carbon moiety to a detoxified polysaccharide from said gram-negative bacterium. The novel immunizing agent of our invention is prepared by a method wherein the lipid A portion of a lipopolysaccharide derived from a gram-negative bacterium is first separated to give a lipid A-free, detoxified polysaccharide, which is selectively oxidized to produce aldehyde groups thereon. The selectively oxidized lipid A-free polysaccharide is covalently coupled through the aldehyde groups to a protein derived from said gram-negative bacterium by means of a 4-12 carbon moiety containing functionalities reactive to the aldehyde group on the lipid A-free polysaccharide and carboxylic acid group on the detoxified protein. The compositions of the invention are useful as vaccines for parenteral administration for preventing bacterial infections and for administration to donors to raise the levels of antibody to a gram-negative bacterium of said donors. Blood collected from such donors may be pooled and fractionated to yield an immune serum globulin having a very high titer of said antibody. The high titer immune serum globulin may be administered to patients suffering from a particular gram-negative bacterial infection.

It is a particular advantage of the compositions of the invention that they exhibit a high degree of immunogenicity free of toxicity or endotoxic activity. Indeed, the immunogenicity of the immunizing agents is nearly equivalent to that of native lipopolysaccharide. By the phrase free of toxicity or endotoxin activity is meant the composition causes no weight loss or failure to gain weight in mice and has less than 1/1000th the activity of lipopolysaccharide in the Limulus amebocyte lysate assay.

It is important to note that the lipid A-free polysaccharide and the detoxified protein individually are not immunogenic. Furthermore, mixtures of the lipid A-free polysaccharide and the detoxified protein are also inactive.

DESCRIPTION OF THE PREFERRED EMBODIMENTS

As mentioned above the immunizing composition of the invention comprises a detoxified protein derived from a gram-negative bacterium covalently coupled by means of a 4-12 carbon moiety to a detoxified polysaccharide from said gram-negative bacterium.

In the following description emphasis will be directed to *Pseudomonas aeruginosa*. This direction is by way of illustration only, not limitation. In its ambit the invention includes immunizing compositions against gram-negative bacteria such as *Escherichia coli, Proteus* sp, *Serratia* sp, *Klebsiella* sp et al.

In a first step in the preparation of an immunizing composition for *P. aeruginosa*, the protein portion of the LPS-protein complexes of the *P. aeruginosa* bacteria are separated from the remaining portion of the complex. This may be accomplished by a variety of known chemical and physical methods. For example, one may use chemical methods such as guanadinium thiocyanate, zwitterionic detergent, lysozyme-ethylene diamene tetraacetic acid, sodium dodecyl sulfate, dimethyl formamide and the like. See, for example, Moldow et al, *J. Membrane Biol.*, 10, 137-152 (1972), Hancock et al, *J. of Bacteriology*, 136, 381-390 (1978), Stinnett et al, ibid., 114, 399-407 (1973), and Robinson et al, *FEMS Microbiol. Lett.*, 5, 131-134 (1979). As examples of physical methods for extracting the protein from the protein-LPS complex, one may use such means as osmotic shock and sonication. Extraction of the protein may also be accomplished by a combination of the aforedescribed procedures.

The extracted or isolated protein is then detoxified. To this end the protein is subjected to mild aqueous alkaline hydrolysis to destroy the toxic components such as enzymes and endotoxin. In general, the concentration of alkali and the temperature and duration of the treatment are sufficient to detoxify the protein, that is, to render the protein non-toxic when administered to humans. As the alkali one may use sodium hydroxide or potassium hydroxide, in water or solvent solution, and the like. Usually, 1 part of the protein is mixed with about 0.1-10.0 parts of 0.1-3.0M alkali. The hydrolysis generally is conducted at a temperature of about 45°-80° C. for a period of about 0.5-5 hours. After heating water is removed from the mixture by conventional techniques such as ultrafiltration, lyophilization, and so forth. It is desirable to remove from the mixture material having a molecular weight of less than about 10,000. This may be accomplished by known methods such as dialysis, ultrafiltration, and the like.

LPS may be isolated from *P. aeruginosa* bacteria by known techniques such as the phenol-water extraction method of Westphal et al, *Z. Naturforach*, 79, 148-155 (1952), trichloroacetic acid (Staub In Meth. Carbohydrate Chem. Vol. 5, pp. 92-93, 1965), aqueous butanol (Leive et al, In Meth. Enzymol Vol. 28, pp. 254-262, 1972) and the like. In the procedure of Westphal et al, LPS is isolated by extraction of *P. aeruginosa* bacteria with a phenol-water mixture. The crude LPS is sonicated and digested with ribonuclease and deoxyribonuclease. After pronase digestion the LPS preparation may be subjected to diafiltration and ultrafiltration to remove low molecular species.

The so-isolated LPS is next subjected to mild acid hydrolysis (Drewry et al, *Biochem. J.*, 149, 93-106, 1975) to remove the lipid A moiety, i.e., to prepare lipid A-free, detoxified polysaccharide. For this purpose one may use acetic acid, hydrochloric acid and the like. Generally, the LPS is mixed with the acid in an aqueous medium in the proportion of about 1-4 parts of acid per part of LPS. For instance, the LPS may be mixed with a 0.5-3% aqueous solution of acid such that the concentration of LPS is about 1-5 mg per ml. The mixture is then heated at a temperature and for a time sufficient to remove the lipid A portion of the LPS, usually about 1-24 hours at 60°-100° C. The precipitate that forms comprises the lipid A portion of the LPS and is separated from the lipid A-free polysaccharide by conventional techniques such as centrifugation, decantation, filtration, and so forth. To assure removal of all lipid A, the supernatant containing the lipid A-free polysaccharide is adjusted to about neutrality and extracted with a chlorohydrocarbon-alcohol mixture.

The aqueous layer containing the lipid A-free polysaccharide is concentrated and the lipid A-free polysaccharide is purified by conventional techniques such as gel filtration, column chromatography and the like and then dried, e.g., by rotary evaporation or lyophilization.

Next, the lipid A-free polysaccharide is selectively oxidized to generate aldehyde groups on the detoxified polysaccharide. This may be accomplished by known procedures such as, for example, periodate oxidation as described by Sanderson et al, *Immunology*, 20, 1061-1065, (1971). Accordingly, the lipid A-free polysaccharide is treated with a source of periodate ions, such as sodium periodate, potassium periodate, etc., in an amount and under conditions sufficient to selectively generate aldehyde groups on the detoxified polysaccharide. Generally, an aqueous solution containing 1-20 mg/ml of detoxified polysaccharide is mixed with 1-100 mM periodate at ambient temperature in the dark for 10-24 hours. The reaction is stopped by addition of ethylene glycol and the selectively oxidized lipid A-free polysaccharide is purified by, for example, column chromatography or gel filtration and then treated to remove water by evaporation, lyophilization, or the like.

The selectively oxidized lipid A-free polysaccharide is coupled to the detoxified protein by means of a 4-12 carbon moiety having functionalities reactive to the aldehyde groups of the polysaccharide and to carboxylic acid groups of the detoxified protein. Accordingly, the detoxified protein is coupled with a 4-12 carbon moiety containing at least two amino groups. Excess amino is generally employed. Thus, for example, about 3-20 parts of amine may be mixed with one part of detoxified protein in a buffered medium (pH 5.0-7.0) at a temperature of about 20°-40° C. for about 1-5 hours. Preferably, it is desirable to carry out the above coupling in the presence of an agent which will promote the coupling of the amino to carboxylic groups on the detoxified proteins. The generally preferred agent is a carbodiimide such as that described by Cuatrecasas, *J. Biol. Chem.*, 245, 3059-3065 (1970). Usually, the carbodiimide is present in an amount of about 0.5-2 parts of amine amount. After the above carbodiimide-promoted amide link reaction, the mixture is treated by conventional means such as dialysis or diafiltration to remove unreacted amine compound and carbodiimide. Preferably, the reaction mixture above is dialyzed against a buffer system compatible with the reaction medium of the subsequent coupling of the derivatized detoxified protein to lipid A-free polysaccharide prepared as described above. Usually, the pH of the buffer system is about 7.0-9.0.

The selectively oxidized lipid A-free polysaccharide is coupled via a Schiff's base reaction to the detoxified protein derivatized with a 4-12 carbon moiety containing an amino group available for reaction with the aldehyde groups on the lipid A-free polysaccharide. In the above coupling it is desirable that the reaction be conducted in the presence of a reducing agent. For this purpose the preferred reducing agent is a cyanoborohydride such as that described by Borch et al, J. Am. Chem. Soc., 93, 2897-2904 (1971). In general, about 1-5 parts of dry lipid A-free polysaccharide and 2-20 parts of cyanoborohydride are mixed with 0.5-3 parts of derivatized detoxified protein in a buffer system of pH about 7.0-9.0. The reaction mixture is then held at about 20°-50° C. for about 24-168 hours. The product comprising the detoxified protein covalently coupled to detoxified, lipid A-free polysaccharide by means of a 4-12 carbon moiety, the detoxified protein being coupled to the 4-12 carbon moiety by means of an amide linkage and the lipid A-free polysaccharide being coupled to the 4-12 carbon moiety by means of amine linkages. This product may be purified by column chromatography, gel filtration, or the like.

The immunizing compositions of this invention are free of detectable endotoxic activity and toxicity but are highly immunogenic. A particular composition may be administered to a host such as a human in an amount effective to induce an immune response to an organism. A particular composition may be administered to a host in an effective amount to prevent infections by gram-negative bacteria to which the composition is directed. The present compositions can be administered individually or in combination. Administration may be subcutaneous, intramuscular, or intracutaneous with or without adjuvant.

The immunizing compositions can be manufactured in the usual method for preparing vaccines for humans and other animals. For example, the immunizing composition may be dissolved in a suitable solvent with or without adjuvant. As the solvent one may use distilled water, physiological saline and phosphate-buffered aqueous sodium chloride solution. Illustrative of adjuvants are aluminum hydroxide, aluminum phosphate, calcium phosphate, alum and Freund's incomplete adjuvant. The amount of adjuvant may be appropriately selected from the range of amounts being necessary and sufficient for increasing the immunoactivity.

An immunizing dose of the present material in mice is 5 μg of low molecular weight ($5\times 10^3$-$4\times 10^4$) polysaccharide conjugated to 14-52 μg of bovine serum albumin or bacterial protein.

An immunizing composition may also be used to produce anti-serum against the gram-negative bacterium to which it is directed. Antibody can be collected from the anti-serum. The anti-serum and antibody can be used to prevent infections caused by the particular gram-negative bacterium. Furthermore, the blood collected from donors vaccinated with the present immunizing composition can be fractionated according to known techniques to yield a hyperimmune serum globulin having a high titer of antibody to a particular gram negative bacterium when compared to an immune serum globulin fractionated from blood obtained from a donor to whom the composition of the invention was not administered. Such immune serum globulin may be administered to a patient intramuscularly or it may be treated by known procedures to render it intravenously injectable. For example, an immunizing composition derived from P. aeruginosa may be administered to donors from whom blood is collected and fractionated to give a hyperimmune gamma globulin. The so-obtained immune serum globulin or gamma globulin may be administered intramuscularly to prevent infection by P. aeruginosa. Alternatively, the hyperimmune serum globulins may be rendered intravenously injectable by methods well known in the art. Such hyperimmune gamma globulins have a titer of antibody against P. aeruginosa of about 1:8,000-≧1:64,000 as determined in the enzyme linked immunosorbent assay (ELISA). These hyperimmune serum globulins were heretofore unavailable. Thus, the invention also comprises pharmaceutical preparations containing an immune serum globulin with an ELISA titer of antibody to a gram-negative bacteria, for example, P. aeruginosa, of about 1:8,000-≧1:64,000.

The term "pharmaceutical preparation" is intended in a broader sense herein to include preparations containing a composition in accordance with this invention used not only for therapeutic purposes, but also for reagent purposes as known in the art or for tissue culture. The pharmaceutical preparation intended for therapeutic use should contain a therapeutic amount of composition, i.e., that amount necessary for preventative or curative health measures. If the pharmaceutical preparation is to be employed as a reagent, then it should contain reagent amounts of composition. Similarly, when used in tissue culture or a culture medium the composition should contain an amount of the present composition sufficient to obtain the desired growth.

EXAMPLES

The invention is demonstrated further by the following illustrative examples.

EXAMPLE 1

Isolation and Detoxification of Protein Derived from P. aeruginosa

P. aeruginosa immunotype 3, American Type Culture Collection (ATCC) 27314 was grown in glucose-glutamine-salts medium. Cells were killed with 0.5% formalin. Killed cells were suspended in 0.01M Tris [hydroxymethyl] amino methane hydrochloride (Tris-HCl) buffer pH 7.8 containing 5 mM ethylene diamine tetraacetic acid (EDTA) and 5 mM β-mercaptoethanol and then sonicated. Disrupted cells and soluble materials were extracted with 6M guanidinium thiocyanate for 18 hours at room temperature. Guanidinium thiocyanate was removed by dialysis against 6M urea. Urea was removed by dialysis against saline. Saline soluble fraction contained the protein.

The saline soluble protein from above was treated with 1M NaOH at 56° C. for 2 hours. Alkali was neutralized with acetic acid. This procedure removed fatty acids ester linked to lipid A, the toxic moiety of contaminating LPS. Detoxified protein was concentrated by ultrafiltration on a PM 10 filter (Amicon, Lexington, MA). Low molecular weight material <10,000 was removed by this process.

The detoxified protein was characterized as follows:
1. No LPS endotoxic activity.
2. Minimal toxicity in mice.
3. Less than 1/1000th of activity of native protein in the Limulus amebocyte lysate assay.
4. Reactive with antisera to both native and detoxified bacterial protein.
5. By HPLC profile (TSK Gel 3000 SW) 80% of the detoxified protein is in the 10–30,000 MW range and 20% ≧ 100,000 MW.

EXAMPLE 2

Coupling of Diaminobutane to Detoxified Protein

Detoxified bacterial protein (14 mg) in 5.0 ml of 0.05M phosphate buffered saline pH 7.2 was coupled with 1,4-diamino butane (300 mg) in the presence of 300 mg 1-(3-dimethyl-amino propyl)-3-ethyl carbodiimide. After 2 hours of gentle stirring at 21° C., the reaction mixture was dialyzed 4 times against 4 liters of 0.05M carbonate buffer pH 8.3 at 4° C. to remove excess reagent. The aminobutyl derivatized detoxified protein was characterized by HPLC (TSK-Gel 4000 sw) as containing about 94% 85,000 MW protein.

EXAMPLE 3

Preparation of Lipid A-free Polysaccharide from *P. aeruginosa*

LPS was isolated from *P. aeruginosa* cells prepared as in Example 1 by the phenol-water extraction procedure of Westphal et al, supra. The water layer containing crude LPS was dialyzed for 3–4 days against distilled water to remove phenol and low molecular weight bacterial substances. The crude LPS was further sonicated for 15 minutes to solubilize LPS micells and digested with ribonuclease and deoxyribonuclease in 0.1M acetate buffer pH 5.0 at 35° C. for 18–24 hours to remove impurities of RNA and DNA. The contaminates of the bacterial protein, ribonuclease and deoxyribonuclease, in LPS were subjected to pronase digestion at pH 7.0 for 24 hours. The LPS was purified by diafiltration and ultrafiltration through Amicon ® hollow fiber cartridge (HIX 50) to remove low molecular weight nucleic acids, peptides, and amino acids.

The purified LPS was treated in 1% acetic acid at a concentration of 2.5 mg/ml and then heated at 87° C. for 18 hours. The lipid A precipitate was removed by centrifugation. The acetic acid supernatant was adjusted to pH 7.0 with NaOH and extracted 3–5 times with two volumes of $CHCl_3$:methanol (2:1 vol./vol.) mixture to remove residual lipid A. The aqueous layer containing polysaccharide was concentrated by rotary evaporation under vacuum. The lipid A-free polysaccharide (PS) was further fractionated on a BioGel-A5m (2.6 cm × 100 cm) column chromatography. The retarded fraction from BioGel-A5m chromatography was further purified on Sephadex ® G-25 (2.6 × 100 cm) column. The major void volume fractions from Sephadex ® G-25 were combined and concentrated by rotary evaporation or lyophilization.

The polysaccharide was characterized as follows:
1. Free of endotoxin (LPS) activity.
2. Absence of toxicity in mice.
3. Less than 1/1000th the activity of LPS in the Limulus amebocyte lysate assay.
4. Reactive with antiserum to LPS in agar gel.
5. Unable to induce antibody or resistance to infection in mice.
6. MW of $5 \times 10^3 - 4 \times 10^4$.

EXAMPLE 4

Selective Oxidation of Polysaccharide

Polysaccharide (2.5 mg/ml) from Example 3 was oxidized with $NaIO_4$ (32 mM) at room temperature in the dark for 19 hours. At the end of reaction, ethylene glycol was added to expend the excess $NaIO_4$, and the solution was left at room temperature for an additional 3–4 hours. The selectively oxidized polysaccharide was further purified by gel filtration (Sephadex ® G-25 column 1.0 cm × 100 cm). The major carbohydrate-content fractions were combined and lyophilized.

The selectively oxidized polysaccharide was characterized as follows:
1. Increased number of aldehyde groups than native polysaccharide.
2. Reactive with antiserum to LPS.
3. No change in MW range.

EXAMPLE 5

Coupling of Selectively-oxidized Polysaccharide and Derivatized Detoxified Protein Lyophilized selectively oxidized PS (10 mg) from Example 4 and 25 mg of sodium cyanoborohydride were dissolved in 2.2 ml of 0.05M $NaHCO_3$, pH 8.3 containing 4.4 mg of derivatized detoxified protein, and the reaction was incubated at 37° C. for 74 hours. The reaction mixture was further purified by gel filtration on Sephadex ® G-100 column (100 cm × 1.0 cm).

The so obtained product was characterized as follows:
1. Purified polysaccharide linked covalently to non-toxic protein.
2. Absence of toxicity in mice.
3. Less than 1/1000th the activity of LPS in the Limulus amebocyte lysate assay.
4. Reactive with antiserum to LPS and detoxified protein.
5. Induces serum antibody and resistance to infection in mice.
6. About 90% in 600,000 MW range.

EXAMPLE 6

Mouse Studies

TABLE 1

Immunogenicity of the components of *P. aeruginosa* immunotype 1 polysaccharide:protein conjugate vaccine

| Immunizing Substance | Dose[a] μg/Mouse | ELISA[b] titer IgG | Cumulative Mortality at 3 days[c] No. dead/total | |
|---|---|---|---|---|
| | | | Active Immunity | Passive Immunity[d] |
| Free polysaccharide | 5.0 | <1:400 | 10/10 | 10/10 |
| Aminobutyl-bovine serum albumin | 38.4 | <1:400 | 8/10 | 8/10 |
| Polysaccharide: albumin conjugate | 5.0: 38.4 | 1:2319 | 3/10[e] | 1/6[e] |
| Polysaccharide and albumin mixture | 5.0 plus 38.4 | <1:400 | 10/10 | 8/10 |

TABLE 1-continued

Immunogenicity of the components of *P. aeruginosa* immunotype 1 polysaccharide:protein conjugate vaccine

| Immunizing Substance | Dose[a] μg/Mouse | ELISA[b] titer IgG | Cumulative Mortality at 3 days[c] No. dead/total | |
|---|---|---|---|---|
| | | | Active Immunity | Passive Immunity[d] |
| Saline | | <1:400 | 8/10 | 10/10 |

[a]Mice immunized by subcutaneous injection on days 1, 7, 14 and 21.
[b]The dilution of serum giving an A° 405 nm of 0.10.
[c]Mice challenged by the intraperitoneal route with 10 times the 50% lethal dose of *P. aeruginosa* immunotype 1-1369.
[d]Serum obtained 3 days after 4th immunization. Mice passively immunized with 0.1 ml serum by the intraperitoneal route.
[e]Statistically significant (P < 0.05 - Fisher's exact test) compared to saline controls.
CONCLUSION:
Resistance to infection and stimulation of passively protective antibody occurs only in mice immunized with the polysaccharide: protein conjugate.

TABLE 2

Induction of passively protective antibody with *P. aeruginosa* immunotype 1 conjugate vaccine

| Day of[a] Immunization (5.0 μg polysaccharide/dose) | Bleeding day after first Immunization | ELISA titer IgG | Cumulative Mortality No. dead/total Passive immunity[b] | |
|---|---|---|---|---|
| | | | Normal Mice | Burned Mice |
| Preimmune | −1 | <1:400 | 9/10 | 10/10 |
| 1 | 6 | <1:400 | 9/10 | 10/10 |
| 7 | 13 | 1:1313 | 6/10 | 6/10[d] |
| 14 | 20 | 1:2481 | 0/10[e] | 3/10[d] |
| 21 | 29 | 1:3808 | 1/10[e] | 1/10[e] |
| | 37 | 1:2482 | 4/10[d] | 3/10[d] |

[a]17 mice immunized with vaccine and bled on days indicated. Immunized mice were challenged 72 days after 4th immunization with 10 times the 50% lethal dose of *P. aeruginosa* 1-1369. Cumulative mortality was 1 of 17 and 8 of 9 in saline immunized controls (P < .0005).
[b]Normal and burned mice given 0.05 ml serum 3 hours before infection. Passively immunized normal mice were challenged with 10 LD$_{50}$.
[c]Pentobarbital anesthetized mice given a 10% dorsal full thickness burn with a gas flame then challenged with 680 cells in 0.5 ml saline by subcutaneous injection in the burn site.
[d]Statistically significant (P < 0.05) protection compared to preimmune serum.
[e](P < 0.001).
CONCLUSION:
1. Highly protective antibody is produced following 3 injections of conjugate vaccine.
2. Active immunity persists for at least 2½ months following immunization.

What is claimed is:

1. An immunizing composition effective against gram-negative bacteria, selected from the group consisting of *Pseudomonas aeruginosa, Proteus* sp, *Serratia* sp, and *Kiebsiella* sp, free from toxicity and endotoxin activity comprising a detoxified protein containing reactive carboxylic acid groups, derived from said gram-negative bacteria, covalently coupled by means of a 4-12 carbon moiety containing at least two amino groups to a lipid A-free polysaccharide having reactive aldehyde groups, wherein there is used about 3-20 parts of amine per 1 part of detoxified protein and about 1-5 parts of dry lipid A-free polysaccharide per 0.5-3 parts of the foregoing derivatized protein.

2. The immunizing composition of claim 1 wherein said detoxified protein is covalently coupled by means of an amide linkage formed by the reaction of a carboxylic acid group on the detoxified protein with an amino group on the 4-12 carbon moiety and the resulting derivatized protein is covalently coupled by means of an amine linkage formed by the reaction of an aldehyde group on the lipid A-free polysaccharide with an amino group on the derivatized protein in the presence of a reducing agent.

3. The composition of claim 1 wherein the gram-negative bacterium is *Pseudomonas aeruginosa.*

4. The composition of claim 1 which further comprises an adjuvant.

5. A pharmaceutical preparation comprising the immunizing composition of claim 1 dissolved in a suitable solvent.

6. A method for preventing infection by gram-negative bacteria, selected from the group consisting of *Pseudomonas aeruginosa, Proteus* sp, *Serrtia* sp, and *Klebsiella* sp, in a host which comprises administering to the human and other animal an effective amount of the composition of claim 1.

7. The method of claim 6 wherein the gram-negative bacterium is *Pseudomonas aeruginosa.*

8. A method of inducing an immune response to a gram-negative bacteria, selected from the group consisting of *Pseudomonas aeruginosa, Proteus* sp, *Serratia* sp, and *Klebsiella* sp, in a host which comprises administering to said host an effective amount of the composition of claim 1.

9. A method for preparing hyperimmune serum globulin having a high titer of antibody to a particular gram-negative bacteria, selected from the group consisting of *Pseudomonas aeruginosa, Proteus* sp, *Serratia* sp, and *Klebsiella* sp, which comprises—
   (a) administering to a donor an amount of the composition of claim 1 derived from said gram-negative bacteria, said amount being sufficient to raise the antibody to said gram-negative bacteria to a level higher than normally found in the blood of said donor,
   (b) obtaining blood from said donor during a period in which the blood of said donor exhibits a higher than normal titer of antibody against said gram-negative bacteria, and
   (c) fractionating said blood to give an immune serum globulin having a high titer of antibody to said gram-negative bacteria when compared to an immune serum globulin fractionated from blood obtained from a donor to whom the composition of claim 1 was not administered.

10. The method of claim 9 wherein the gram-negative bacterium is *Pseudomonas aeruginosa.*

11. A hyperimmune serum globulin produced by the method of claim 9 having a titer of antibody to said gram-negative bacteria of about 1:8,000-≧1:64,000.

12. A method of treating an infection in a human caused by gram-negative bacteria, selected from the group consisting of *Pseudomonas aeruginosa, Proteus* sp, *Serratia* sp, and *Klebsiella* sp, which comprises administering to said human an effective amount of the hyperimmune serum globulin produced by the method of claim 9.

13. A method for preparing the composition of claim 1, which comprises—
   (a) separating the lipid A portion of a lipopolysaccharide derived from said gram-negative bacteria, selected from the group consisting of *Pseudomonas aeruginosa, Proteus* sp, *Serretia* sp, and *Klebsiella* sp, to give a lipid A-free polysaccharide,
   (b) selectively oxidizing the lipid A-free polysaccharide to produce reactive aldehyde groups thereon,
   (c) detoxifying protein derived from said gram-negative bacteria to obtain a detoxified protein containing reactive carboxylic acid groups, and
   (d) covalently coupling said detoxified protein to said selectively oxidized lipid A-free polysaccharide by means of a 4-12 carbon moiety containing at least two amino groups reactive to said detoxified protein and to said selectively oxidized lipid A-free polysaccharide.

14. The method of claim 13 wherein the 4-12 carbon moiety contains at least two amino groups and the detoxified protein is coupled thereto by means of an amide linkage and the lipid A-free polysaccharide is coupled thereto by means of an amine linkage.

15. The method of claim 13 wherein the gram-negative bacterium is *Pseudomonas aeruginosa*.

16. An immunizing composition effective against *Pseudomonas aeruginosa* free from toxicity and endotoxin activity comprising a detoxified protein, selected from the group consisting of (a) a detoxified protein having reactive carboxylic acid groups, derived from *Pseudomonas aeruginosa* and (b) bovine serum albumin having reactive carboxylic acid groups, covalently coupled by means of a 4-12 carbon moiety containing at least two amino groups to a lipid A-free polysaccharide having reactive aldehyde groups, wherein there is used about 3-20 parts of amine per 1 part of detoxified protein and about 1-5 parts of lipid A-free polysaccharide per 0.5-3 parts of the foregoing derivatized protein.

* * * * *